(12) United States Patent
Fraser

(10) Patent No.: US 6,432,106 B1
(45) Date of Patent: *Aug. 13, 2002

(54) ANTERIOR LUMBAR INTERBODY FUSION CAGE WITH LOCKING PLATE

(75) Inventor: Robert Fraser, Myrtle Bank (AU)

(73) Assignee: DePuy AcroMed, Inc., Raynham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/449,105

(22) Filed: Nov. 24, 1999

(51) Int. Cl.$^7$ ................................. A61B 17/70

(52) U.S. Cl. ..................... 606/61; 606/60; 623/17.16

(58) Field of Search ................ 623/16.11, 17.11, 623/17.16; 606/60, 61, 69

(56) References Cited

U.S. PATENT DOCUMENTS

| | | | | |
|---|---|---|---|---|
| 4,599,086 A | * | 7/1986 | Doty | 623/17 |
| 4,743,256 A | | 5/1988 | Brantigan | 623/17 |
| 4,834,757 A | | 5/1989 | Brantigan | 623/17 |
| 4,878,915 A | | 11/1989 | Brantigan | 623/17 |
| 5,192,327 A | | 3/1993 | Brantigan | 623/17 |
| 5,306,309 A | * | 4/1994 | Wagner et al. | 623/17 |
| 5,397,364 A | | 3/1995 | Kozak et al. | 623/17 |
| 5,425,772 A | | 6/1995 | Brantigan | 623/17 |
| 5,443,515 A | | 8/1995 | Cohen et al. | 623/17 |
| 5,522,899 A | | 6/1996 | Michelson | 623/17 |
| 5,607,424 A | | 3/1997 | Tropiano | 606/61 |
| 5,658,335 A | * | 8/1997 | Allen | 623/17 |
| 5,658,337 A | | 8/1997 | Kohrs et al. | 623/17 |
| 5,716,415 A | | 2/1998 | Steffee | 623/17 |
| 5,755,798 A | | 5/1998 | Papavero et al. | 623/17 |
| 5,766,252 A | | 6/1998 | Henry et al. | 623/17 |
| 5,776,199 A | | 7/1998 | Michelson | 623/17 |
| 5,782,832 A | | 7/1998 | Larsen et al. | 606/61 |
| 5,800,550 A | | 9/1998 | Sertich | 623/17 |
| 5,824,094 A | * | 10/1998 | Serhan et al. | 623/17 |
| 5,861,041 A | | 1/1999 | Tienboon | 623/17 |
| 5,865,845 A | | 2/1999 | Thalgott | 623/17 |
| 5,888,227 A | | 3/1999 | Cottle | 623/17 |
| 5,888,228 A | | 3/1999 | Knothe et al. | 623/17 |
| 5,904,683 A | * | 5/1999 | Pohndorf et al. | 606/61 |
| 5,961,554 A | | 10/1999 | Janson et al. | 623/17 |
| 5,964,807 A | * | 10/1999 | Gan et al. | 623/17 |
| 5,976,187 A | | 11/1999 | Richelsoph | 623/17 |
| 6,019,793 A | * | 2/2000 | Perren et al. | 623/17 |
| 6,045,579 A | * | 4/2000 | Hochshuler et al. | 623/17 |
| 6,080,193 A | * | 6/2000 | Hochshuler et al. | 623/17 |
| 6,093,205 A | * | 7/2000 | McLeod et al. | 623/17 |
| 6,096,080 A | * | 8/2000 | Nicholson et al. | 623/17 |
| 6,113,638 A | * | 9/2000 | Williams et al. | 623/17 |
| 6,120,503 A | * | 9/2000 | Michelson | 606/61 |
| 6,156,037 A | * | 12/2000 | LeHuec et al. | 606/61 |
| 6,168,596 B1 | * | 1/2001 | Wellisz | 606/69 |
| 6,176,882 B1 | * | 1/2001 | Biedermann et al. | 623/17.15 |
| 6,231,610 B1 | * | 5/2001 | Geisler | 623/17.11 |
| 6,235,069 B1 | * | 5/2001 | Benezech et al. | 623/17.16 |

FOREIGN PATENT DOCUMENTS

| | | |
|---|---|---|
| DE | 29511146 | 6/1995 |
| FR | 2742653 | 12/1995 |
| FR | 2747034 | 4/1996 |
| WO | WO 97/20526 | 6/1997 |
| WO | WO 99/63914 | 12/1999 |

* cited by examiner

Primary Examiner—Jeffrey A. Smith
Assistant Examiner—Michael B. Priddy
(74) Attorney, Agent, or Firm—Nutter McClennan & Fish LLP

(57) ABSTRACT

A spinal fixation assembly includes a fusion cage to which a plate is mated. The plate is configured to receive, retain and orient bone screws.

33 Claims, 3 Drawing Sheets

ANTERIOR LUMBAR INTERBODY FUSION CAGE WITH LOCKING PLATE

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates to medical devices, and more particularly to an implantable structure for promoting fusion of adjacent vertebral bodies.

BACKGROUND OF THE INVENTION

Advancing age, as well as injury, can lead to changes in the bones, disks, joints, and ligaments of the spine producing pain from nerve root compression. Under certain circumstances, alleviation of pain can be provided by performing a spinal fusion. This is a procedure that involves joining two or more adjacent vertebrae so that they no longer are able to move relative to each other.

Many prosthetic devices are known for promoting fusion of the spinal vertebrae, and the devices can be classified, in part, based upon the approach to the spine that will be taken by the surgeon (anterior, posterior, lateral, etc.). None of the known devices is completely satisfactory, and improvements are desirable.

SUMMARY OF THE INVENTION

The present invention improves upon known spinal fusion devices, especially those devices intended for an anterior approach to the spine. In an exemplary embodiment, a spinal fixation assembly includes a fusion cage to which a plate is mated. The plate is configured to receive, retain and orient bone screws, thereby holding the fusion cage and adjacent vertebral bodies in a stable relationship to promote fusion.

Additional features of the assembly can include a plate mated to the fusion cage so as to be slidable therewith, and joining them with a mortise and a tenon. The plate can include extensions or tabs through which bone screws are passed and retained on one or both of the superior and inferior sides of the fusion cage. The tabs can be angled to orient the screws as desired.

The fusion cage can include convex superior and inferior surfaces, and it can be tapered from the anterior face to the posterior face. Both the fusion cage and the plate can include insertion tool guide and engagement features, such as bores and notches. Fins can be provided at one or more points on the inferior and superior faces of the fusion cage.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

Figure 1:
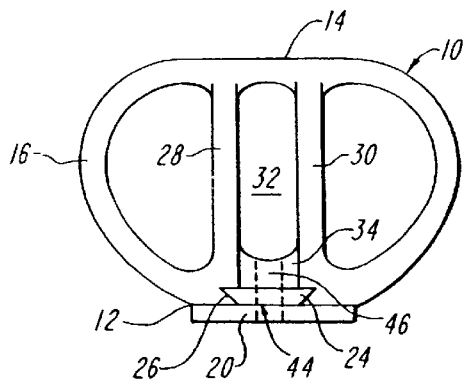
FIG. 1 is a plan view of a fusion cage in accordance with the present invention.

FIG. 1 is a plan view of a fusion cage in accordance with the present invention. The cage includes a body 10 that approximates the shape and size of the annulus portion of a disk which normally separates two vertebral bodies. The body 10 includes faces that are named in relation to their orientation with respect to a patient. Specifically, the body 10 includes an anterior face 12, a posterior face 14, a superior face 16, and an inferior face 18 (visible in FIG. 2). Except where specifically noted, as used herein, "face" is not intended to connote the outwardmost surface ("face surface" is used) or a specific geometry (e.g., planar). Rather, "face" refers to a general region on different sides of the body 10. A carbon fiber composite or other radiolucent material is well suited for fabrication of the body.

Figure 2:
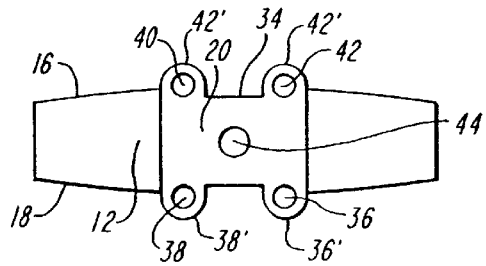
FIG. 2 is a view of the anterior face of the fusion cage of FIG. 1.
Figure 3:
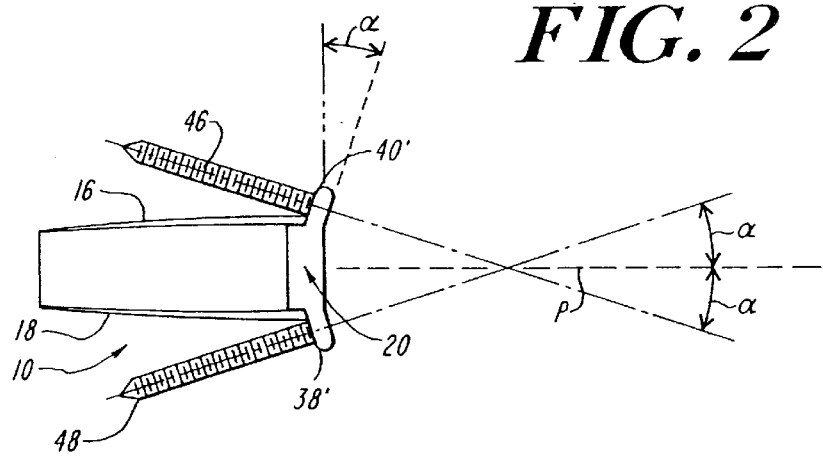
FIG. 3 is a side view of the fusion cage of FIG. 1 with bone screws.

The cage further includes a plate 20 that is matable with the body 10. Titanium or carbon fiber composites are suitable materials for the plate 20. As shown in FIGS. 1, 2, and 3, the plate 20 is mated with the anterior face 12 of the body 10 for an anterior approach to the spine. However, other embodiments of the fusion cage are configured for mating the plate 20 to the body 10 at locations other than the anterior face 12 as required for an anterolateral or lateral approach to the spine.

Although the plate 20 can be bonded firmly to the body 10 so that the plate and body cannot move with respect to each other, they can also be mated to allow movement with respect to each other. For example, in the illustrated embodiment, the plate 20 includes a tenon 24 that is disposed within a mortise 26 defined by the body 10, wherein the tenon can slide in a superior/inferior direction within the mortise.

Continuing to refer to FIG. 1, the fusion cage can also be provided with first and second transverse elements 28 and 30, respectively, that join the posterior face 14 to the anterior face 12. The transverse elements 28 and 30 enhance the structural integrity of the body 10 and provide additional load bearing surface. The transverse elements 28 and 30 can also be configured to provide a guide path for a fusion cage insertion tool. For example, the guide path in the illustrated embodiment is between the transverse elements in the space numbered 32. The guide path can further include a notch or depression 34 in one or both of the superior face 16 or inferior face 18 of the body or defined by the plate 20 as shown in FIG. 2. In an exemplary embodiment, the guide path is about 8 mm wide and recessed about 1 mm to 2 mm below the superior/inferior face surface.

Referring now to FIG. 2, an embodiment of the plate 20 is shown mated to the anterior face 12. In this illustration, four bone screw holes 36, 38, 40 and 42 are visible as is a guide bore or hole 44. The guide hole 44 is aligned with a bore 46 (shown in FIG. 1) in the body 10. Both the guide hole 44 and the bore 46 are configured to receive a portion of an insertion tool (not shown), and both the guide hole and bore can be provided with tool engagement features such as threads. As shown, the bone screw holes 36, 38, 40 and 42 can be disposed in or defined by plate extensions or tabs 36', 38', 40' and 42', wherein the tabs and the remainder of the plate 20 can all lie in the same plane, or one or more of the tabs can be angled with respect to the remainder of the plate or one or more of the other tabs.

Turning to FIG. 3, bone screws 46 and 48, each having a head and a shank are shown disposed through the holes in tabs 40' and 38', respectively, such that the head of each screw engages the respective tab to inhibit passage of the head through the aperture in the tab. In an exemplary embodiment, the screws are about 3.6 mm in diameter and about 22 mm in length. The screws are of the "locking" type, so that they cannot "back out" of the holes in the plate.

Continuing to refer to FIG. 3, tabs 38' and 40' are shown angled with respect to the remainder of the plate 20 so that screws 46 and 48 are angled with respect to the medial plane "P" of the body 10. The angle formed by the tab(s) and plate, as well as by the screw(s) and medial plane, is designated as "α" and is determined by a particular situation and a patient's anatomy. Although the angle "α" can range from 15° to 60°, for most applications the angle "α" is about 20°. However, in other embodiments, the tabs are flexible or readily bent with respect to the remainder of the plate 20.

Also shown in FIG. 3 are other advantageous features of the fusion cage, such as flat to slightly convex inferior and superior face surfaces 18 and 16, respectively, and a slightly tapered (about 10°) or wedge profile, wherein the body 10 is thicker at the anterior face 12 than at the posterior face 14.

Figure 4:
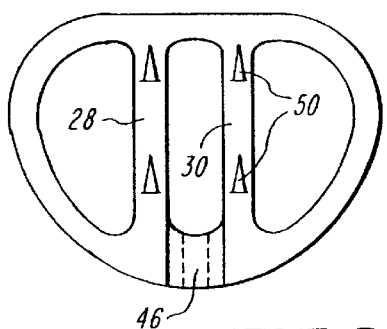
FIG. 4 is a plan view of an embodiment of a fusion cage in accordance with the invention having fins on the superior face of the cage.
Figure 5:
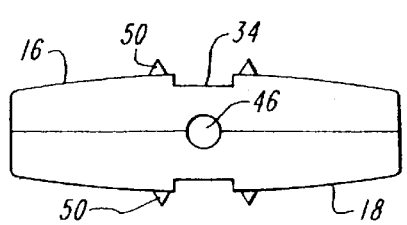
FIG. 5 is a view of the anterior face of the fusion cage of FIG. 4.
Figure 6:
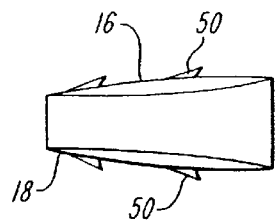
FIG. 6 is a side view of the fusion cage of FIG. 4.
Figure 10:
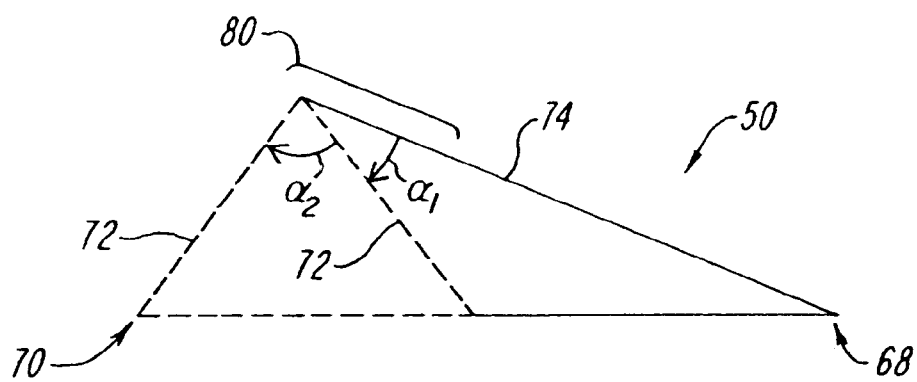
FIG. 10 is a side elevation view of a bone engagement fin in accordance with the invention.
Figure 11:
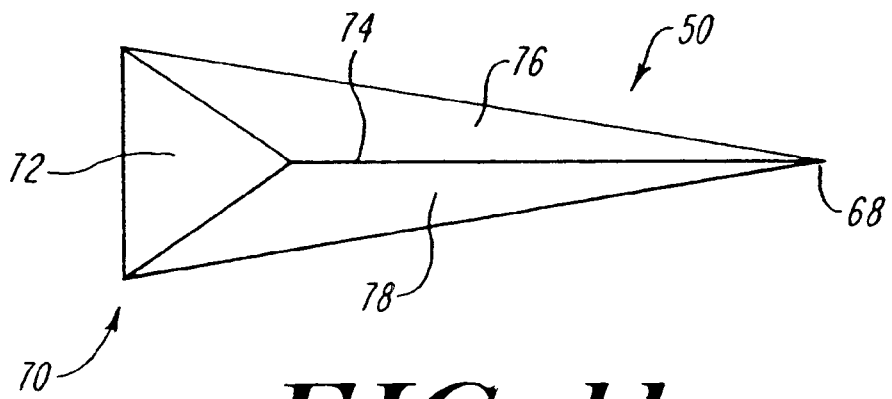
FIG. 11 is a top view of an exemplary bone engagement fin.

Referring now to FIG. 4, a fusion cage is shown with sharp fins 50 on the superior face of the transverse elements 28 and 30. As shown in FIGS. 5 and 6, fins 50 can also be provided on the inferior face of the transverse elements 28 and 30. Exemplary fins are about 1 mm to 2 mm in height. FIGS. 10 and 11 illustrate exemplary fins in greater detail. As shown in FIG. 10, an exemplary fin 50 has a first end 68 and a second end 70, and as illustrated in FIG. 4, each fin is oriented in a generally anterior/posterior so that the first end is closer to the posterior face 14 of the fusion cage and the second end is closer to the anterior face 12. One or more fins can be tapered so that the second end 70 is taller than the first end 68 which merges flush with the face of the cage on which it is formed or mounted. Also, as shown in FIGS. 4 and 11, the second end 70 can be wider than the first end 68 which comes to a point.

Continuing to refer to FIG. 10, a posterior face 72 can be angled during manufacture to provide a range of fin configurations. When an angle defined by the posterior face 72 and a line 74 formed by the intersection of opposing fin sides 76 and 78 is small (e.g., $\alpha_1$,) a top fin portion 80 forms a "spike" that readily will dig into bone if the fin is moved toward the second end 70. If, as shown by dotted lines in FIG. 10, and from above in FIG. 11, the angle defined by the posterior face 72 and a line 74 formed by the intersection of opposing fin sides 76 and 78 is larger (e.g., $\alpha_2$) a top fin portion 80 forms a "spike" that readily will dig into bone when the fin and bone are pressed toward each, as when the fusion cage is compressed between two vertebral bodies.

The fusion cage of FIGS. 4, 5 and 6 does not include a plate 20, but it does include a bore 46 for engaging an insertion tool, as well as a guide path or groove. Additional advantages of the present invention are evident when the invention is viewed in context.

Figure 7:
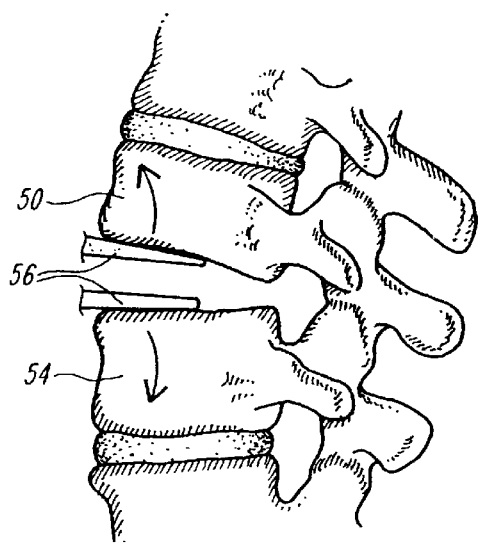
FIG. 7 illustrates adjacent vertebral bodies being separated in preparation for insertion of a fusion cage.

FIG. 7 is a lateral view of adjacent vertebral bodies 52 and 54 being distracted or separated with a surgical implement 56, of which only the distal portion is visible, in preparation for insertion of a fusion cage in accordance with the invention, the disk having been removed and the implant area prepared.

Figure 8:
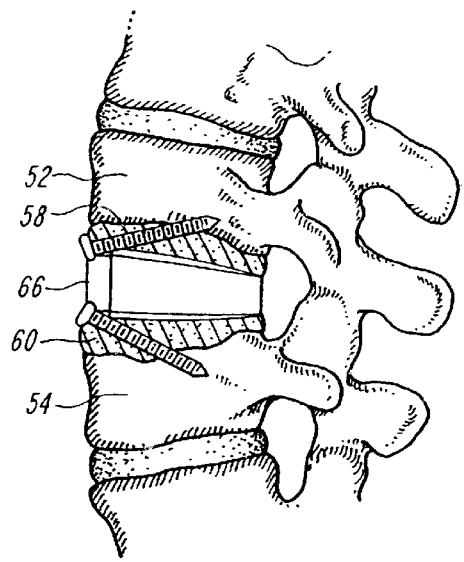
FIG. 8 depicts a portion of the spine following placement of the fusion cage of FIG. 1.

FIG. 8 depicts the fusion cage described above with respect to FIGS. 1, 2 and 3 after it has been implanted. In this view, portions of the vertebral bodies are shown cut-away to illustrate the penetration of the bone screws 58 and 60 into the bodies. It is important to note that screw heads 62 and 64 are flush or sub-flush with the anterior face surface 66 of the fusion cage, thus minimizing the likelihood that major blood vessels running along the spine will be injured.

Figure 9:
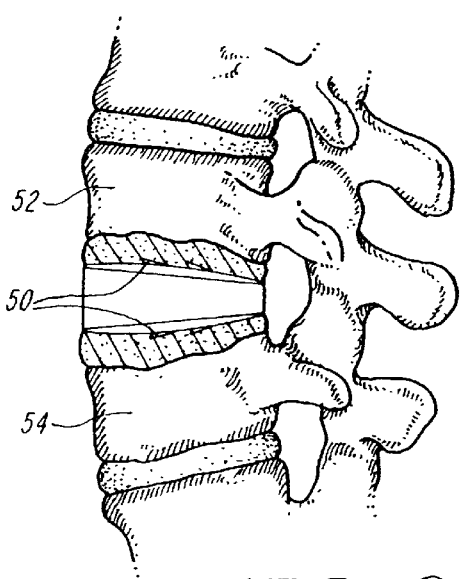
FIG. 9 depicts a portion of the spine following placement of the fusion cage of FIG. 4.

FIG. 9 illustrates the fusion cage described above with respect to FIGS. 4, 5 and 6 after it has been implanted. In this view, portions of the vertebral bodies are shown cut-away to illustrate the penetration of the fins 50 into the vertebral bodies 52 and 54. It should be noted that because the fins 50 can be tapered both in height and width. Thus, the tapering, in combination with the anterior/posterior orientation of the fins, allows the fusion cage to be inserted between the vertebral bodies with minimal resistance due to the fins, thereby minimizing necessary distraction distance between vertebral bodies. Also, the raised second end of the fins significantly inhibits anterior movement of the fusion cage once it has been positioned between vertebral bodies, as it "digs-in" to the vertebral bone if the fusion cage is urged in an anterior direction. In other words, the fins enhance purchas and provide expusion protection.

Prior to inserting a fusion cage between vertebral bodies, the space bounded by the body 10 and transverse elements 28 and 30 (if included) can be filled with autograft or allograft bone, or demineralized bone matrix (DBM) to promote fusion. Over a period of about three months the vertebral bodies fuse.

As should be readily apparent from the preceding description, the present invention provides many advantages. For example, the fusion cage is sufficienty broad and thick so that only a single cage is needed to replace an excised disk. The profile and slightly bowed or convex superior and inferior surfaces of the fusion cage body closely approximate the shape of a natural disk and provide an excellent, stable, load-bearing surface. The plate, when included, ensures that the body will not become dislodged from the spine, yet is readily accessible with an anterior approach. Further, the plate allows bone screws to be deeply embedded into the vertebral bodies without piercing or otherwise damaging the hard, load-bearing, cortical bone. Also, both the plate and the body include features that allow for relatively easy manipulation and insertion with appropriately configured surgical tools.

Of course, one skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal fixation assembly comprising:
    a fusion cage having
        a posterior face,
        an anterior face,
        a superior face, and
        an inferior face;
    a plate slidably engaged with the fusion cage so as to be movable in a superior/inferior direction with respect to the fusion cage, the plate defining at least one tab having an aperture for receiving a bone screw, the at least one tab being angled with respect to the fusion cage in a direction anterior to the anterior face of the fusion cage; and
    a bone screw having a head and a shank, the shank being dimensioned to pass through the aperture in the plate, and the head being dimensioned to engage the plate to inhibit passage of the head through the aperture in the plate.

2. The spinal fixation assembly of claim 1, wherein the plate is mated to the anterior face of the fusion cage.

3. The spinal fixation assembly of claim 1, wherein the plate and the fusion cage are joined with a mortise and a tenon.

4. The spinal fixation assembly of claim 1, wherein the fusion cage includes a medial plane that separates the inferior face from the superior face to define an inferior side and a superior side, and wherein the plate defines a first aperture on a first tab on the inferior side of the fusion cage and a second aperture on a second tab on the superior side of the fusion cage.

5. The spinal fixation assembly of claim 4, wherein the first tab and the second tab are flexible.

6. The spinal fixation assembly of claim 4, wherein one of the first tab and the second tab is angled with respect to the plate at an angle between 15° and 60°.

7. The spinal fixation assembly of claim 4, wherein one of the first tab and the second tab is angled with respect to the plate at an angle of about 20°.

8. The spinal fixation assembly of claim 4, wherein the fusion cage defines a bore centered on the medial plane and open at the anterior face.

9. The spinal fixation assembly of claim 8, wherein the plate defines a bore therethrough that is aligned with the bore defined by the fusion cage.

10. The spinal fixation assembly of claim 1, wherein one of the superior face and the inferior face is convex.

11. The spinal fixation assembly of claim 1, wherein the fusion cage is thicker at the anterior face than at the posterior face.

12. The spinal fixation assembly of claim 11, wherein the fusion cage tapers at about 10° from the anterior face to the posterior face.

13. The spinal fixation assembly of claim 11, wherein the fusion cage defines an annulus with a first transverse element and a second transverse element.

14. The spinal fixation assembly of claim 13, wherein the first and second transverse elements extend from the anterior face to the posterior face.

15. The spinal fixation assembly of claim 14, wherein the first transverse element is substantially parallel to the second transverse element.

16. The spinal fixation assembly of claim 1, further including a plurality of fins extending outward from the fusion cage on one of the superior face and the inferior face.

17. The spinal fixation assembly of claim 1, further including a notch on one of the superior face and inferior face that extends from the anterior face toward the posterior face.

18. A spinal fixation assembly comprising:
    a fusion cage having
        a posterior face,
        an anterior face,
        a superior face, and
        an inferior face;
    a plate mated to the anterior face of the fusion cage and having an inferior extension and a superior extension, the plate defining a first aperture in the inferior extension and a second aperture in the superior extension; and
    at least one bone screw having a head and a shank, the shank being dimensioned to pass through the aperture in the plate, and the head being dimensioned to engage the plate to inhibit passage of the head through the aperture in the plate; and
    wherein the inferior and superior extensions are angled with respect to the fusion cage in a direction anterior to the anterior surface of the fusion cage.

19. The spinal fixation assembly of claim 18, wherein one of the superior face and the inferior face is convex and wherein the fusion cage is thicker at the anterior face than at the posterior face.

20. The spinal fixation assembly of claim 19, wherein the fusion cage tapers at about 10° from the anterior face to the posterior face.

21. The spinal fixation assembly of claim 19, wherein the fusion cage defines an annulus with a first transverse element and a second transverse element.

22. The spinal fixation assembly of claim 21, wherein the first and second transverse elements extend from the anterior face to the posterior face.

23. The spinal fixation assembly of claim 22, wherein the first transverse element is substantially parallel to the second transverse element.

24. The spinal fixation assembly of claim 18, wherein the plate is slidably engaged with the fusion cage so as to be movable in a superior/inferior direction.

25. The spinal fixation assembly of claim 24, wherein the plate and the fusion cage are joined with a mortise and a tenon.

26. The spinal fixation assembly of claim 18, wherein the inferior extension is a first tab that defines the first aperture and the superior extension is a second tab that defines the second aperture.

27. The spinal fixation assembly of claim 26, wherein the first tab and the second tab are flexible.

28. The spinal fixation assembly of claim 26, wherein one of the first tab and the second tab is angled with respect to the plate at an angle between 15° and 60°.

29. The spinal fixation assembly of claim 26, wherein one of the first tab and the second tab is angled with respect to the plate at an angle of about 20°.

30. The spinal fixation assembly of claim 18, wherein the fusion cage includes a medial plane and defines a bore centered on the medial plane and open at the anterior face.

31. The spinal fixation assembly of claim 30, wherein the plate defines a bore therethrough that is aligned with the bore defined by the fusion cage.

32. The spinal fixation assembly of claim 18, further including a plurality of fins extending outward from the fusion cage on one of the superior face and the inferior face.

33. The spinal fixation assembly of claim 18, further including a notch on one of the superior face and inferior face that extends from the anterior face toward the posterior face.

* * * * *

UNITED STATES PATENT AND TRADEMARK OFFICE
CERTIFICATE OF CORRECTION

PATENT NO. : 6,432,106 B1 Page 1 of 1
DATED : August 13, 2002
INVENTOR(S) : Robert Fraser It is certified that error appears in the above-identified patent and that said Letters Patent is hereby corrected as shown below:

<u>Title page,</u>
Item [56], References Cited, U.S. PATENT DOCUMENTS, should include
-- 5,713,899 A  2/1998  Marnay et al. ………….. 606/61 --

Signed and Sealed this

Twenty-ninth Day of July, 2003

JAMES E. ROGAN
*Director of the United States Patent and Trademark Office*